(12) United States Patent
Burnett

(10) Patent No.: US 9,782,510 B1
(45) Date of Patent: Oct. 10, 2017

(54) PHOTOCATALYTIC DEVICE WITH MULTI-METALLIC CATALYSTS

(71) Applicant: Dust Free, LP, Royse City, TX (US)

(72) Inventor: Gregg William Burnett, Royse City, TX (US)

(73) Assignee: DUST FREE, LP, Royce City, TX (US)

( * ) Notice: Subject to any disclaimer, the term of this patent is extended or adjusted under 35 U.S.C. 154(b) by 156 days.

(21) Appl. No.: 13/745,132

(22) Filed: Jan. 18, 2013

(51) Int. Cl.
*A61L 9/20* (2006.01)

(52) U.S. Cl.
CPC .................................. *A61L 9/205* (2013.01)

(58) Field of Classification Search
CPC ....................................................... A61L 9/205
USPC ........................................ 422/120, 24, 123
See application file for complete search history.

(56) References Cited

U.S. PATENT DOCUMENTS

| | | |
|---|---|---|
| 4,859,329 A | 8/1989 | Fink |
| 5,011,609 A | 4/1991 | Fink |
| 5,120,435 A | 6/1992 | Fink |
| 5,236,585 A | 8/1993 | Fink |
| 5,919,422 A | 7/1999 | Yamanaka et al. |
| 6,221,314 B1 * | 4/2001 | Bigelow ................... 422/24 |
| 6,315,963 B1 * | 11/2001 | Speer ..................... 422/186.3 |
| 6,546,883 B1 | 4/2003 | Fink et al. |
| 6,730,265 B2 * | 5/2004 | Horton, III ............... 422/24 |
| 6,752,970 B2 | 6/2004 | Schwartz et al. |
| 6,784,440 B2 | 8/2004 | Fink et al. |
| 6,949,228 B2 | 9/2005 | Ou Yang et al. |
| 6,997,185 B2 | 2/2006 | Han et al. |
| 7,160,566 B2 | 1/2007 | Fink et al. |
| 7,635,659 B2 | 12/2009 | Naganuma et al. |
| 7,871,518 B2 | 1/2011 | Ellis et al. |
| 7,988,923 B2 | 8/2011 | Fink et al. |
| 2003/0077211 A1 | 4/2003 | Schwartz et al. |

(Continued)

FOREIGN PATENT DOCUMENTS

| | | |
|---|---|---|
| CN | 2392106 Y | 8/2000 |
| CN | 2922905 Y | 7/2007 |

(Continued)

OTHER PUBLICATIONS

"Cylinder". Random House Kenerman Webster's College Dictionary. 2010.*

(Continued)

*Primary Examiner* — Donald Spamer
(74) *Attorney, Agent, or Firm* — Fogarty LLP

(57) ABSTRACT

A photocatalytic device has an ultraviolet light source and a plurality of photocatalytic structures, such as hydrated metallic catalyst surfaces. One or more catalyst substrates are adapted to support a hydroxyl radical reaction with ultraviolet light and water vapor that results in hydro peroxides and hydroxyl ions; an ultraviolet light source provides ultraviolet light to the catalyst substrates. The catalyst substrates comprising a hydrated multi-metallic catalyst having two or more elements or compounds selected from the group: Titanium dioxide, Titanium Platinum, Gold, Silver, Copper, Rhodium, Ruthenium, Lanthanum, Carbon, and Fluoride. In different embodiments, various combinations of these elements or compounds may be used in the catalyst, such as a combination of five or more of the elements or compounds.

19 Claims, 6 Drawing Sheets

(56) References Cited

U.S. PATENT DOCUMENTS

| | | |
|---|---|---|
| 2003/0150708 A1 | 8/2003 | Fink |
| 2003/0230477 A1 | 12/2003 | Fink et al. |
| 2004/0016887 A1 | 1/2004 | Fink et al. |
| 2004/0056201 A1 | 3/2004 | Fink et al. |
| 2004/0156959 A1 | 8/2004 | Fink et al. |
| 2004/0170537 A1* | 9/2004 | Hara .................. 422/122 |
| 2004/0197243 A1 | 10/2004 | Schwartz et al. |
| 2005/0186124 A1 | 8/2005 | Fink et al. |
| 2005/0238551 A1* | 10/2005 | Snyder ............ A61L 9/205 422/186.3 |
| 2006/0144690 A1 | 7/2006 | Fink et al. |
| 2006/0163135 A1* | 7/2006 | Ellis et al. .............. 210/251 |
| 2006/0228275 A1 | 10/2006 | Rutman et al. |
| 2006/0266221 A1 | 11/2006 | Fink et al. |
| 2007/0110860 A1 | 5/2007 | Fink et al. |
| 2009/0041617 A1* | 2/2009 | Lee ........................ 422/4 |
| 2009/0183943 A1 | 7/2009 | Leistner et al. |
| 2009/0217690 A1 | 9/2009 | Silderhuis |
| 2011/0250125 A1 | 10/2011 | Fink et al. |

FOREIGN PATENT DOCUMENTS

| | | |
|---|---|---|
| CN | 101245939 A | 8/2008 |
| CN | 201135626 Y | 10/2008 |
| DE | 20211178 U1 | 11/2002 |
| WO | WO 2006/134149 A1 | 12/2006 |

OTHER PUBLICATIONS

"Curve" American Heritage Dictionary of the English Language, Fifth Edition. Houghton Mifflin Harcourt Publishing Company. 2011.*

Vincent. "Answered: Can you describe a square with 1 equation?". Mar. 1, 2010.*

\* cited by examiner

PHOTOCATALYTIC DEVICE WITH MULTI-METALLIC CATALYSTS

TECHNICAL FIELD

Embodiments of the invention are directed, in general, to oxidation technology for air purification systems and, more specifically, to a system for distributing ultraviolet light to a photocatalyst having a plurality of catalytic elements.

BACKGROUND

Ultraviolet light can be used in heating, ventilation, and air conditioning (HVAC) systems to significantly reduce the amount of microbials in ductwork and air space, which helps to reduce possible health problems associated with inhaling microbials. Ultraviolet light (UV) is also beneficial in keeping HVAC coils free of mold, which increases system efficiency.

A typical HVAC system is used to maintain indoor air quality; however, the primary function of most HVAC systems is to control the temperature and humidity of the air. Many indoor air pollutants, such as volatile organic compounds (VOCs), cannot be removed by typical HVAC systems. Often, an air cleaning device may be added to HVAC systems to remove these VOCs. Photocatalytic air cleaning devices are a common technique for indoor air purification and deodorization. A photocatalytic air cleaning device in an HVAC system typically comprises an ultraviolet lamp that illuminates a photocatalytic filter to create free radicals that reduce VOCs.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, a photocatalytic device comprises an ultraviolet light source and one or more catalyst substrates that are adapted to support a hydroxyl radical reaction with water vapor that results in hydro peroxides and hydroxyl ions. The catalyst substrates comprise a hydrated quad-metallic catalyst or any other appropriate catalyst.

The catalyst substrates comprise a hydrated multi-metallic catalyst having two or more elements or compounds selected from the group: Titanium dioxide, Platinum, Gold, Silver, Copper, Rhodium, Ruthenium, Lanthanum, Carbon, and Fluoride. In different embodiments, various combinations of these elements may be used in the catalyst, such as a combination of five or more of the elements.

BRIEF DESCRIPTION OF THE DRAWINGS

Figure 1:
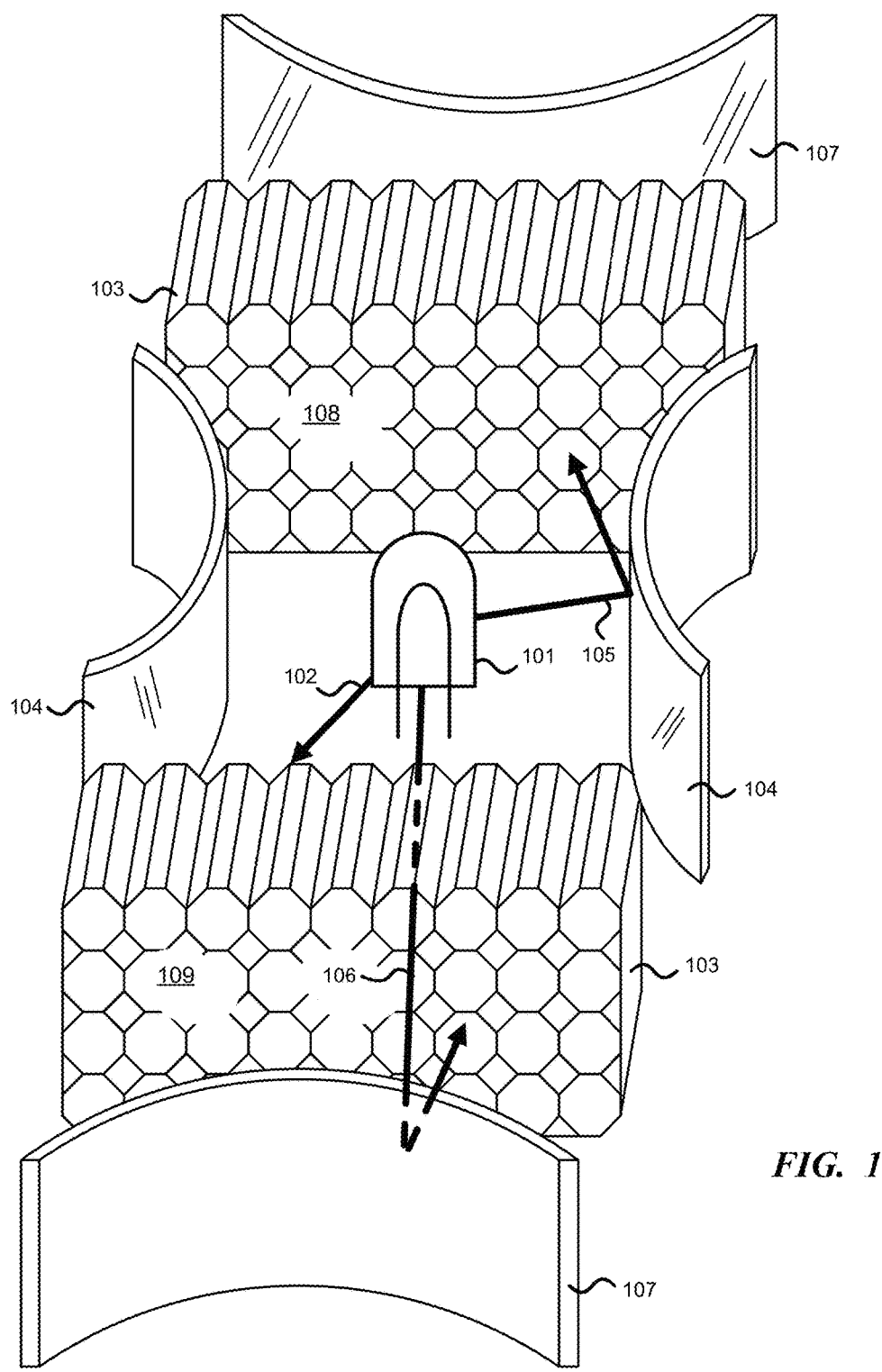
Figure 2:
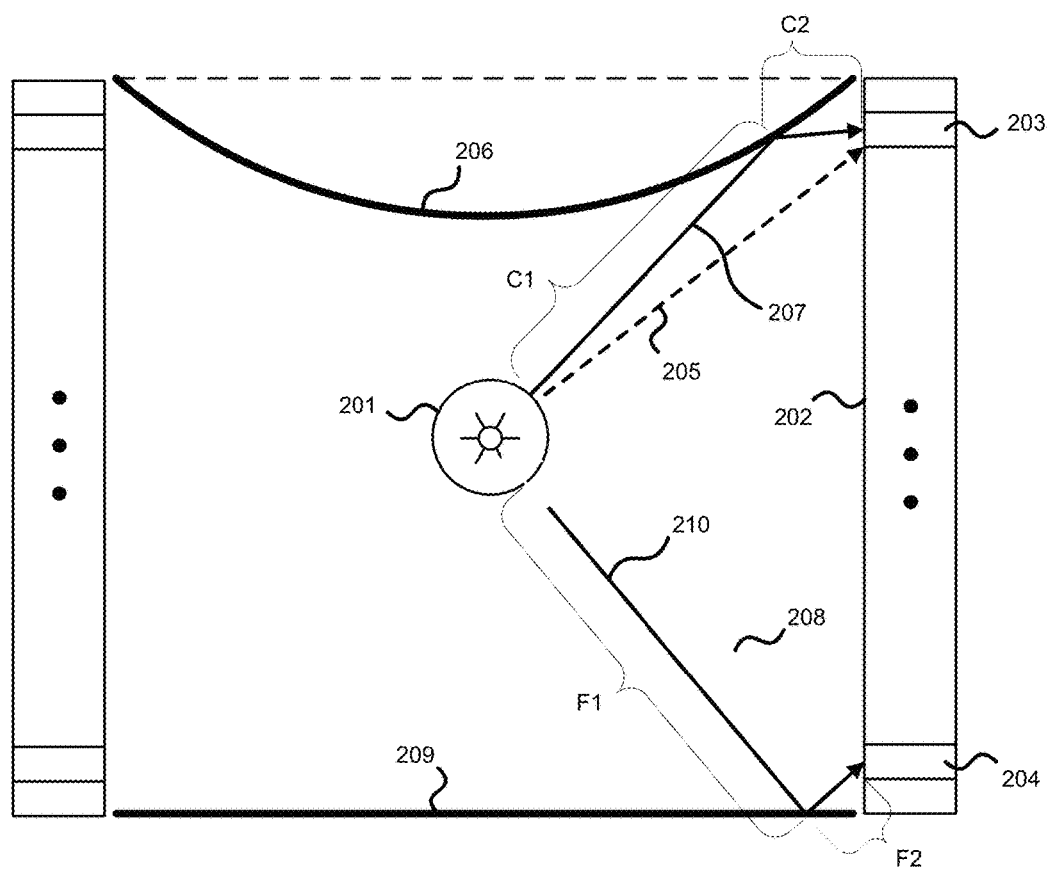
Figure 3:
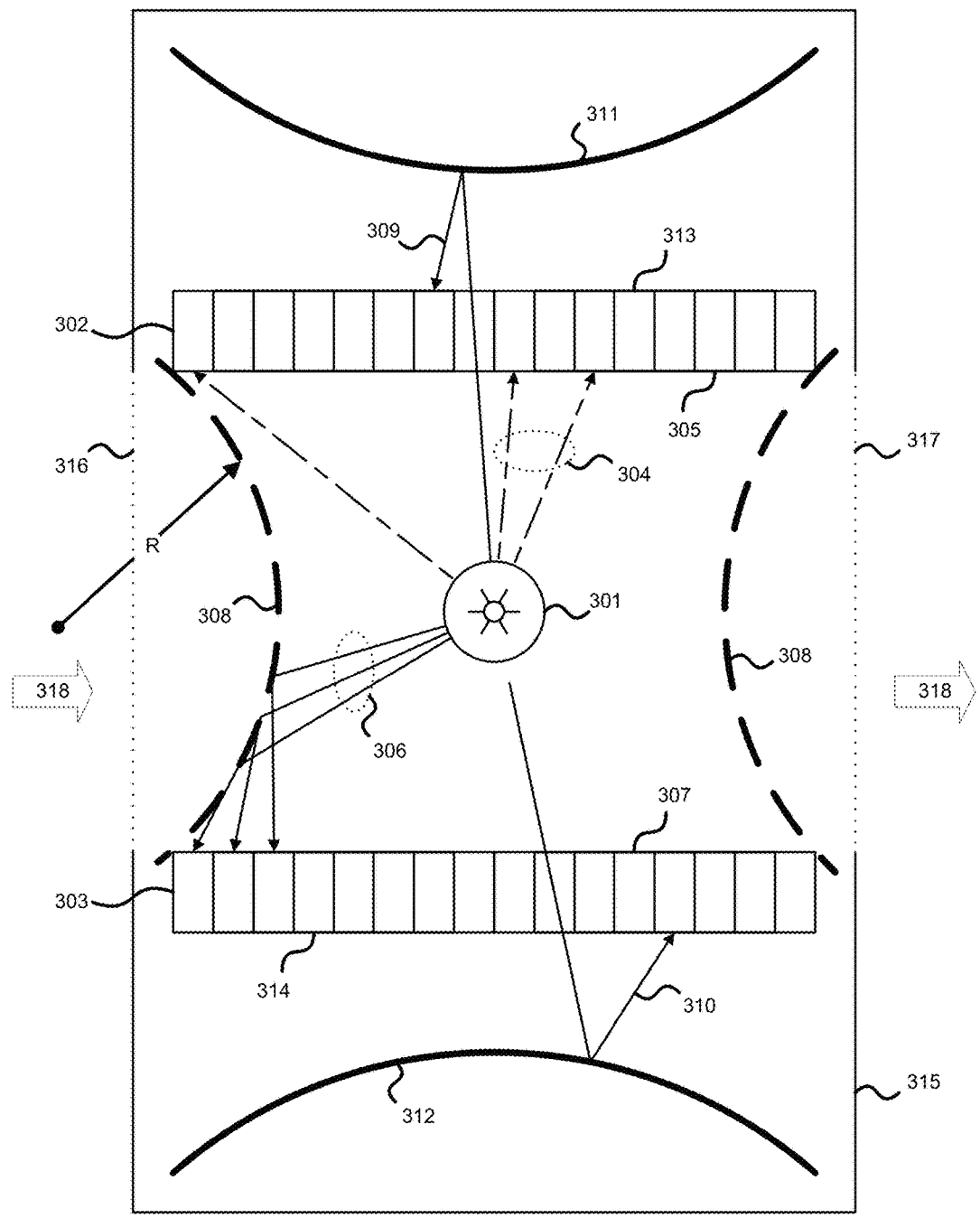
Figure 4:
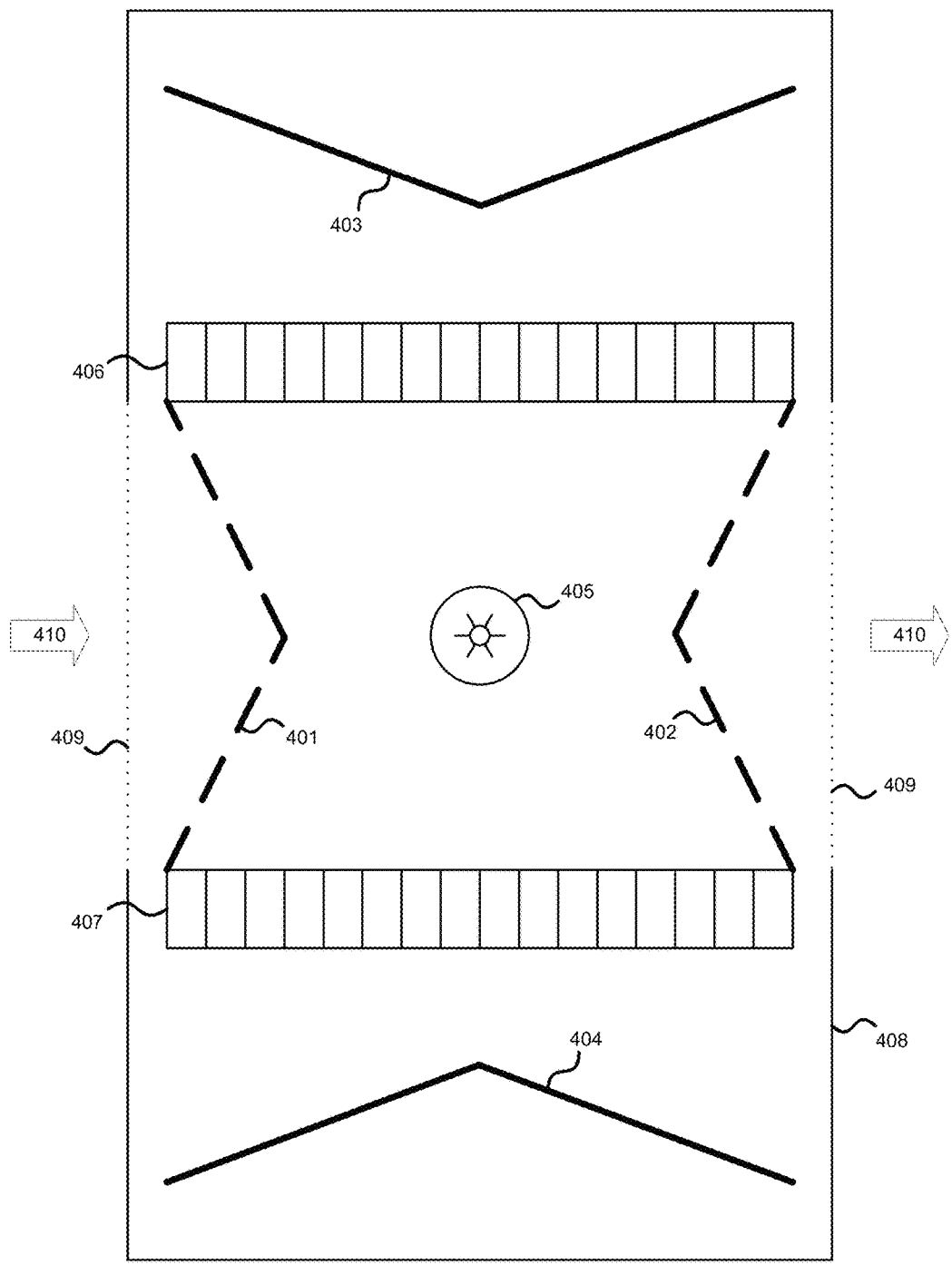
Figure 5:
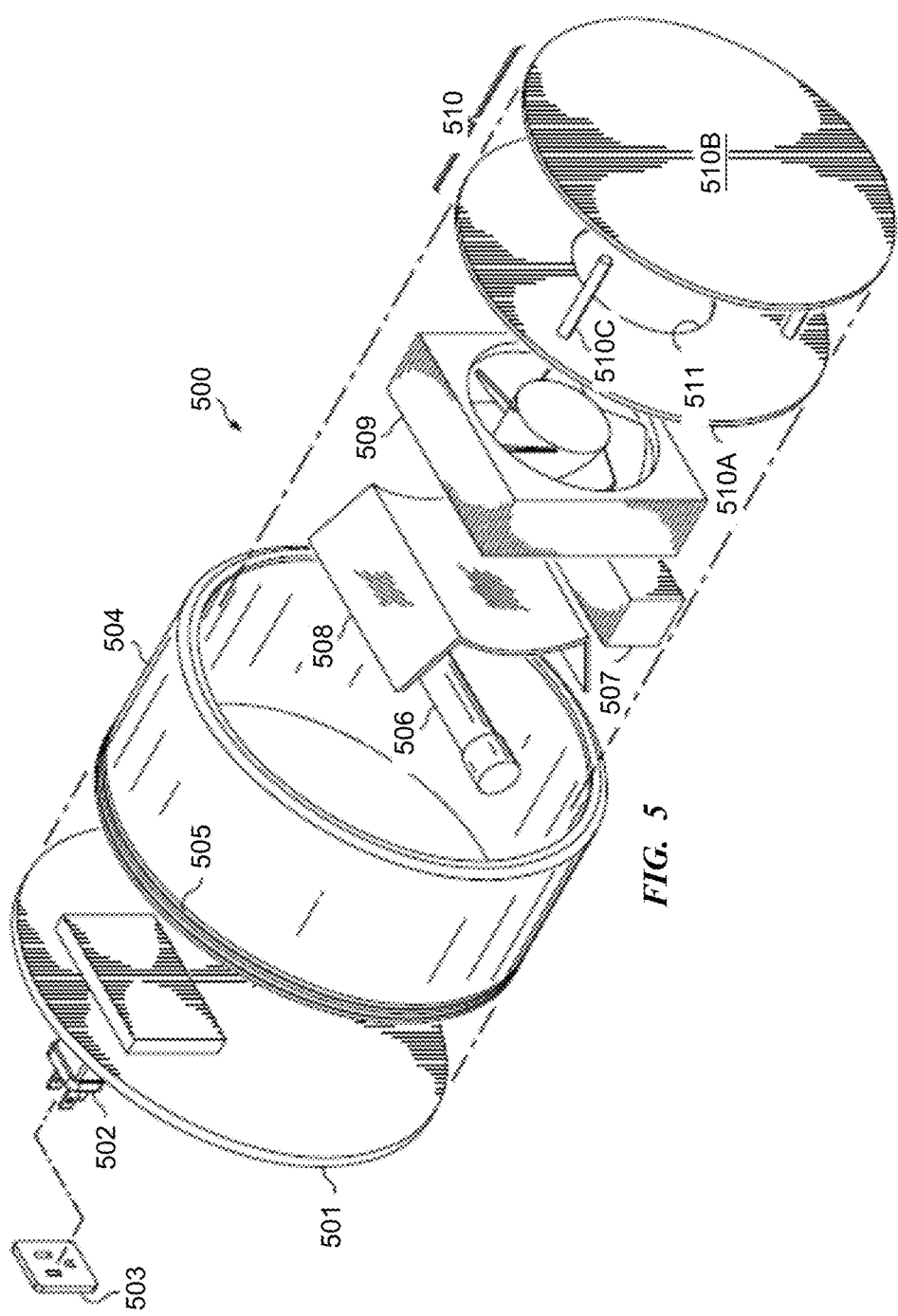
Figure 6:
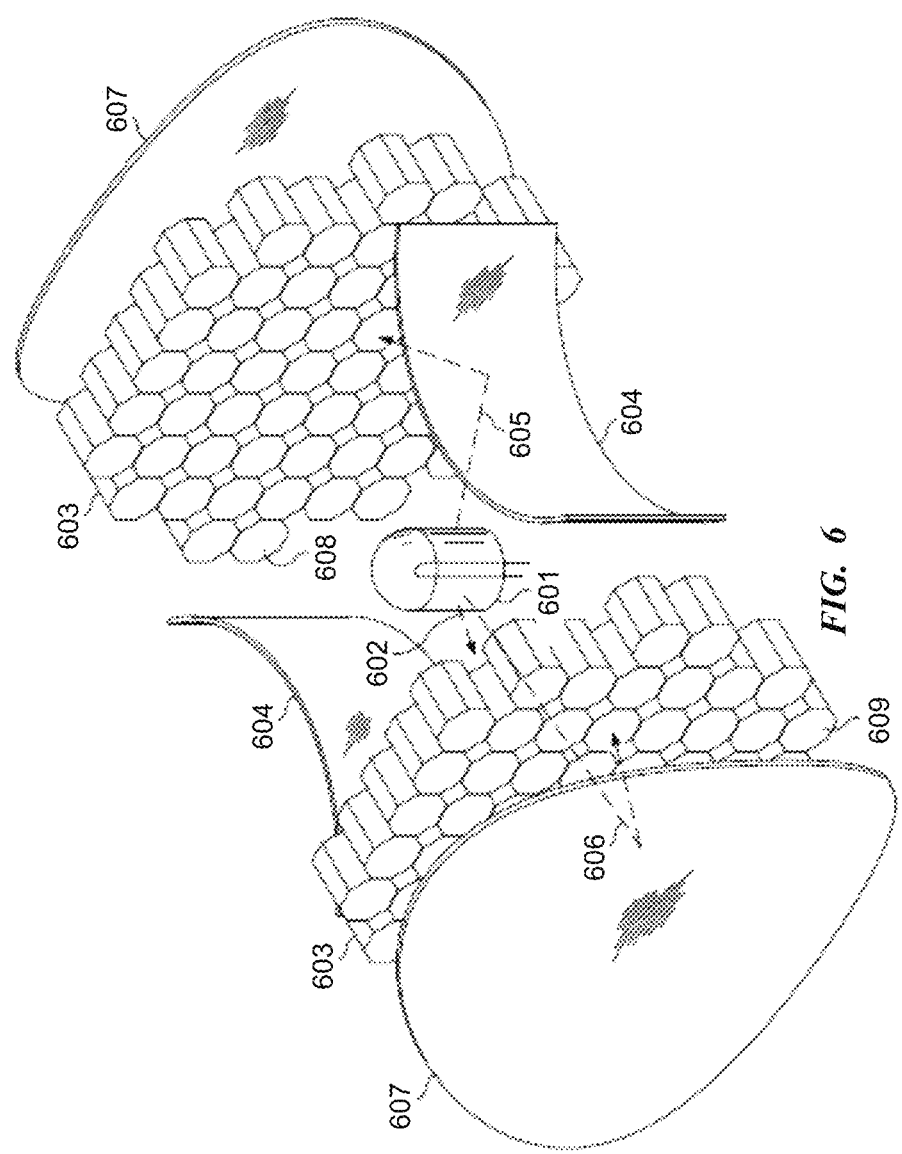

Having thus described the invention in general terms, reference will now be made to the accompanying drawings, which are not necessarily drawn to scale, and wherein:

FIG. 1 is a block diagram illustrating one embodiment of a photocatalytic device;

FIG. 2 is a block diagram illustrating advantages of a curved reflector as used in embodiments of the photocatalytic device described herein;

FIG. 3 is a block diagram illustrating the illumination of opposed surfaces of a target structure according to one embodiment;

FIG. 4 is a block diagram illustrating an alternative embodiment of a photocatalytic device;

FIG. 5 is an exploded view of a photocatalytic device according to an alternate embodiment; and FIG. 6 is a block diagram illustrating elements of a photocatalytic device according to an alternate embodiment.

DETAILED DESCRIPTION

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. A person of ordinary skill in the art will be able to use the various embodiments of the invention.

FIG. 1 is a block diagram illustrating one embodiment of a photocatalytic device. An ultraviolet light source 101 generates ultraviolet light 102. One or more photocatalytic structures 103 are positioned near the ultraviolet light source 101 and are illuminated by the ultraviolet light 102. In one embodiment, the photocatalytic structures 103 comprise a plurality of fluted structures arranged in a honeycomb formation.

The photocatalytic structures 103 may be, for example, a hydrated catalytic matrix, such as a hydrated metallic catalyst. When the ultraviolet light 102 impacts the photocatalytic structures 103, ozone is produced in the catalytic matrix. The catalyst supports a hydroxyl radical reaction with water vapor that results in hydro peroxides, hydroxyl ions, super oxide ions, passive negative ions hydroxides, and ozonide ions. These are highly reactive chemical species. The hydroxyl radicals are very strong oxidizers and will attack organic materials. This creates oxidation that helps to reduce odors, volatile organic compounds (VOCs), airborne viruses, bacteria, mold and other types of air pollution.

The hydrated catalytic matrix 103 may comprise any catalytic compound, element, or combination thereof. In one embodiment, the hydrated catalytic matrix may be a hydrated multi-metallic catalyst multi-metallic catalytic matrix. One such multi-metallic catalytic matrix may be a multi-metallic catalytic matrix comprising one or more of: Titanium, Titanium dioxide, Platinum, Gold, Silver, Copper, Rhodium, Ruthenium, and Lanthanum, for example. In other embodiments, other combinations of rare and noble metals may be used for the catalytic matrix. Additional elements, such as Carbon and/or Fluoride, may also be included in the catalytic matrix. In other embodiments, different combinations of rare and noble metals may be used for the catalytic matrix in various combinations.

Titanium dioxide may be used for water and air treatment as well as for catalytic production of gases. For example, Titanium dioxide may be used as a photocatalyst for the remediation of contaminated water because it is highly active under UV irradiation, stable, non-toxic, and inexpensive. The properties of Titanium dioxide, such as surface area, surface charge, crystallinity, surface crystalline plane, particle size, density of surface functional groups, and lattice defects, influence the photocatalytic activities in a complex way. The surface property of Titanium dioxide is particularly important in determining the photocatalytic reaction kinetics, mechanisms, and efficiencies because the photocatalytic reactions mostly take place on the surface. The surface modification of Titanium dioxide include polymer coating, metal deposition, anion complexation, and hybridization with silica. Such modifications of the Titanium dioxide surface enhance the photocatalytic efficiencies, change the reaction mechanisms, or alter the distribution of intermediates and products.

Each surface modification method has its unique role in affecting the kinetics and mechanisms of photocatalytic reactions. The Platinization of Titanium dioxide (e.g., $Pt/TiO_2$) exhibits enhanced activities for many photocatalytic reactions. It is believed that Platinum deposits on Titanium dioxide attract and hold electrons with retarding their recombination with holes. Moreover, Titanium dioxide modified with both Fluoride and Platinum (e.g., F—$TiO_2$/Pt) exhibits a unique photocatalytic activity for the anoxic degradation of phenolic compounds and the $H_2$ production accompanied by the degradation of phenolic compounds. Other elements, such as Carbon, may also be used in the photocatalytic structures.

In some embodiments, the photocatalytic destruction of organics begins with its excitation by supra-band-gap photons, and continues through redox reactions where OH radicals, formed on the photocatalyst surface, play a major role. The presence of Gold and Platinum in the vicinity of Titanium dioxide may improve the performance of the photocatalyst. This effect has been attributed to a better charge separation between the photo-induced charge carriers and to an ability of the metal to prevent the deactivation of the photocatalyst, probably by a spillover mechanism that supplies oxygen to the Titanium dioxide surface. In addition to Platinum, other metallic elements may be used as catalysts either alone or in combination with other elements. For example, Ruthenium and Lanthanum may also be used as catalysts alone or in combination with other metals.

Embodiments of the photocatalytic structures disclosed herein will be understood to include any one or any combination of two or more of the above referenced elements in a hydrated catalytic matrix. For example, a multi-metallic catalytic matrix may comprise one or more of: Titanium dioxide, Platinum, Gold, Silver, Copper, Rhodium, Ruthenium, and Lanthanum. Additional elements, such as Carbon and/or Fluoride, may also be included in the catalytic matrix. In one embodiment, the catalytic matrix is a hydrated quad-metallic catalyst comprising four or more of the above listed elements (not necessarily all metals). In another embodiment, the catalytic matrix is a hydrated quintuple-metallic catalyst comprising five or more of the above listed elements. Additional embodiments comprise higher order—metallic catalysts (e.g., sextuple-metallic, septuple-metallic, etc.).

Ultraviolet light source 101 may be, for example, a high-intensity, broad-spectrum ultraviolet bulb or tube. In other embodiments, the ultraviolet source may be a low pressure fluorescent quartz bulb or a medium pressure amalgam lamp. Ultraviolet light falls in the band of light between 185 nm and 400 nm. There are three distinct bands of light within the ultraviolet spectrum: UV-A, UV-B, and UV-C. Longwave UV light (315 nm to 400 nm), or UV-A, refers to what is commonly called "black light." Midrange UV (280 nm to 315 nm), or UV-B, causes sunburn. Germicidal UV light (185 nm to 280 nm), or UV-C, is effective in microbial control. Research has demonstrated that the most efficient frequency for microbial destruction is between 254 nm and 265 nm within the UV-C band. Germicidal lamps that produce the majority of their output in this range will be the most effective in microbial control/destruction.

One or more curved reflectors 104 are positioned to reflect ultraviolet light 105 from ultraviolet light source 101 to the face 108 of photocatalytic structures 103. As a result, photocatalytic structures 103 receive both direct ultraviolet light from source 101 and reflected ultraviolet light 105 from curved reflectors 104.

Some ultraviolet light 106 passes through photocatalytic structures 103. Additional curved reflectors 107 are positioned so that ultraviolet light 106 is reflected back to photocatalytic structures 103 on the face 109 opposite ultraviolet light source 101.

In one embodiment, reflectors 106 and 107 are curved in a manner that optimizes the distribution of ultraviolet light across the faces 108, 109 of photocatalytic structures 103.

FIG. 2 is a block diagram illustrating advantages of a curved reflector as used in embodiments of the photocatalytic device described herein. The inverse-square law of light results in a rapid drop-off in the intensity of ultraviolet light as it is radiated away from the light source. The intensity of light waves radiating from a light source is inversely proportional to the square of the distance from the light source. This affects the amount of energy provided to surfaces that are illuminated by the light source. For example, a far surface that is twice as far away from a light source as a near surface, receives only one-quarter of the energy that is received by the near surface. Accordingly, it is important to minimize the distance traveled by the ultraviolet light in the photocatalytic device.

Light source 201 that broadcasts light on target surface 202, which includes a plurality of segments 203, 204. Segment 203 receives light directly from source 201, as illustrated by ray 205. Segment 203 also receives light indirectly from source 201 after reflection from curved reflector 206, as illustrated by ray 207. The light 207 reflected off of curved reflector 206 has a total distance C1+C2.

Segment 204 receives light directly from source 201, as illustrated by ray 208. Segment 204 also receives light indirectly from source 201 after reflection from flat reflector 209, as illustrated by ray 210. The light 210 reflected off of flat reflector 209 has a total distance F1+F2. As illustrated in FIG. 2, the distance traveled by ray 210 is longer than the distance traveled by ray 207. Therefore, the ray 207 from curved reflector 206 will have a higher intensity and higher energy level when it reaches segment 203 when compared to the intensity and energy level of ray 210 when it reaches segment 204.

In addition to minimizing the distance traveled by ray 207, curved reflector 206 also causes the reflected ray to impact the target surface 202 in a perpendicular or nearly perpendicular direction. On the other hand, ray 210 reflected off of flat reflector 209 impact the target surface 202 at an acute angle. Where segments 203, 204 are hollow structures, such as fluted segments of a honeycomb substrate, the perpendicular rays 207 will better illuminate the interior of the segment 203 compared to ray 210's illumination of segment 204.

FIG. 3 is a block diagram illustrating the illumination of opposed surfaces of a target structure according to one embodiment. Ultraviolet light source 301 generates broadband ultraviolet light that illuminates target structures 302, 303. Ultraviolet light rays 304 impact a near side 305 of target structure 302. Reflected rays 306 also impact the near side 307 of target structure 303. Reflective surface 308 is shaped to optimize the impact of reflected rays 306 against near surface 307. The curvature R of reflective surface 308 is selected so that reflected rays 306 travel an optimized minimum distance between source 301 and surface 307.

The curvature R of reflective surface 308 may be of a constant radius, such as in a cross-section of a cylindrical surface. In other embodiments, the curvature R of reflective surface 308 may have a variable radius, such as in a cross-section of a paraboloid or ellipsoid. In other embodiments, the curvature of reflective surface 308 has a radius that varies both in a vertical and horizontal direction.

Some ultraviolet light, such as rays 309, 310, may pass through target structures 302, 303 when those structures are comprised of hollow segments. Reflective surfaces 311, 312 reflect rays 309, 310 back against the far surface 313, 314 of the target structures 302, 303. Reflective surfaces 311, 312 are shaped to optimize the impact of reflected rays 309, 310 against near surface 307. Like surface 308, the curvature of reflective surfaces 311, 312 are selected so that reflected rays 309, 310 travel an optimized minimum distance between source 301 and surfaces 313, 314. The curvature of reflective surfaces 311, 312 may be of a constant radius or a variable radius and/or a radius that varies both in a vertical and horizontal direction.

The photocatalytic device may include an enclosure 315 that protects and/or supports the components, including ultraviolet source 301, reflectors 308, 311, 312, and target structures 302, 303. Enclosure 315 may include ventilated or perforated sections 316, 317 to allow air (318) to flow through the device. Additionally, reflectors 308 may be ventilated or perforated to allow air to flow through the device, thereby allowing for the distribution of hydro peroxides, hydroxyl ions, or other ions into a ventilation system or room.

FIG. 4 is a block diagram illustrating an alternative embodiment of a photocatalytic device. As illustrated in FIGS. 1-3, the reflectors in the photocatalytic device are generally of a curved, convex shape. FIG. 4 illustrates an alternative reflector configuration in which bent reflectors 401-404 have a convex shape, but the reflectors are not curved. The reflectors 401-404 serve the same purpose as reflectors 308, 311, 312 (FIG. 3) wherein ultraviolet light from source 405 is reflected against the surfaces of target structures 406, 407.

Bent reflectors 401-404 may be preferable to curved reflectors under certain manufacturing conditions, for example. The size, shape and angle of bent reflectors 401-404 are selected to optimize the uniform distribution of ultraviolet light across the surfaces of target structures 406, 407. It will be understood that other convex shapes may also be used for the reflectors in other embodiments.

The photocatalytic device may have an enclosure 408 with ventilated sections 409. Additionally, reflectors 401, 402 may be ventilated in order to improve airflow 410 through the photocatalytic device.

Turning to FIG. 5, an exploded view of photocatalytic device 500 according to some embodiments. As illustrated, photocatalytic device 500 may include plate 501, upon which electrical element(s) 502 may be mounted. For example, for example, electrical element(s) 502 may include a plug configured to be coupled to a standard electrical outlet and/or it may include one or more voltage regulators and/or converters configured to obtain electrical power from outlet 503 (or from a battery) and to provide it to one or more of device 500's internal components. Housing or enclosure 504 (e.g., a cylindrical or approximately cylindrical housing) may be mounted onto plate 501, and may include one or more inlet openings 505 (e.g., a grill, a vent, etc.). Internal components assembled within housing 504 may include ultraviolet light source 506, one or more photocatalytic structures 507, one or more reflectors 508, and fan 509. The arrangement and inter-relationship of these components may vary in different embodiments. Generally, ultraviolet light from source 506 shines on photocatalytic structure(s) 507 either directly or after reflection off of reflector(s) 508.

Diffuser assembly 510 may be coupled to housing 504 and may be adapted to spread or distribute the air exiting housing 504 via outlet opening 511. For example, diffuser 510 may include two or more plates, inner plate 510A having outlet opening 511 and an outer plate 510B. As illustrated, the two or more plates may be coupled to each other via one or more columns 510C that provide spacing between these elements. In other embodiments, however, outer plate 510B may be flat and/or configured to allow additional photocatalytic device(s) similar to device 500 to be stacked or mounted upon device 500, thereby increasing the collective air processing capacity of the system.

In operation, photocatalytic device 500 may be used in an upright (on a flat surface, vertical stand, etc.) or horizontal position (plugged directly into and supported by outlet 503, horizontal stand, etc.). When powered (e.g., via outlet 503, a battery, etc.), fan 509 may cause air to enter housing 504 via inlet opening 505, circulate through one or more catalyst substrates 507, and exit housing 504 via an outlet opening 511. Ultraviolet light may be provided by ultraviolet light source 506, and catalyst substrates 507 may be adapted to support a hydroxyl radical reaction with the ultraviolet light and water vapor that results in hydro peroxides and hydroxyl ions within photocatalytic device 500. These hydro peroxides and hydroxyl ions are circulated into the local environment by the air flowing through housing 504.

In some embodiments, one or more of plate 501, housing 504, and/or diffuser 510 may be built with a thermoplastic material such as, for example, polyethylene, polypropylene, polystyrene, polyvinyl chloride, polytetrafluoroethylene (PTFE), etc. Additionally or alternatively, these elements may be built with thermosetting polymers or the like. In other embodiments, one or more of plate 501, housing 504, and/or diffuser 510 may be built with a metal or metal alloy material.

FIG. 6 is a block diagram illustrating elements of a photocatalytic device according to some embodiments. An ultraviolet light source 601 generates ultraviolet light 602, and it may be similar to ultraviolet source 101 discussed in FIG. 1. One or more photocatalytic structures 603 are positioned near ultraviolet light source 601 and are illuminated by the ultraviolet light 602. In an embodiment, the photocatalytic structures 603 may include a plurality of fluted structures arranged in a honeycomb formation.

Photocatalytic structures 603 may be, for example, a hydrated catalytic matrix. When ultraviolet light 602 impacts the photocatalytic structures 603, ozone is produced in the catalytic matrix. The catalyst may support a hydroxyl radical reaction with water vapor that results in hydro peroxides, hydroxyl ions, super oxide ions, passive negative ions hydroxides, and ozonide ions.

Photocatalytic structures 603 will be understood to include any one or any combination of two or more of the above referenced elements or compounds in a hydrated catalytic matrix. For example, a multi-metallic catalytic matrix may comprise one or more of: Titanium, Titanium dioxide, Platinum, Gold, Silver, Copper, Rhodium, Ruthenium, and Lanthanum. Additional elements, such as Carbon and/or Fluoride, may also be included in the catalytic matrix. In one embodiment, the catalytic matrix is a hydrated quad-metallic catalyst comprising four or more of the above listed elements or compounds (not necessarily all metals). In another embodiment, the catalytic matrix is a hydrated quintuple-metallic catalyst comprising five or more of the above listed elements. Additional embodiments comprise higher order—metallic catalysts (e.g., sextuple-metallic, septuple-metallic, etc.).

One or more curved reflectors 604 are positioned to reflect ultraviolet light 605 from ultraviolet light source 601 to the face 608 of photocatalytic structures 603. As a result, photocatalytic structures 603 receive both direct ultraviolet light from source 601 and reflected ultraviolet light 605 from curved reflectors 604.

Some ultraviolet light 606 passes through photocatalytic structures 603. Additional curved reflectors 607 are positioned so that ultraviolet light 606 is reflected back to photocatalytic structures 603 on the face 609 opposite ultraviolet light source 601.

In an embodiment, reflectors 606 and 607 are curved in a manner that increases and/or optimizes the distribution of ultraviolet light across the faces 608 and 609 of photocatalytic structures 603.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

What is claimed is:

1. A photocatalytic device, comprising:
an ultraviolet light source;
two or more catalyst substrates adapted to support a hydroxyl radical reaction with ultraviolet light and water vapor that results in hydro peroxides and hydroxyl ions, wherein the two or more catalyst substrates comprise a hydrated multi-metallic catalyst having one or more compounds or elements selected from the group: Titanium dioxide, Platinum, Gold, Silver, Copper, Rhodium, and one or more elements selected from the group: Titanium, Ruthenium, and Lanthanum, two of the two or more catalyst substrates are positioned on opposite sides of the ultraviolet light source such that a near surface of a first catalyst substrate faces a near surface of a second catalyst substrate; and
at least first and second reflective surfaces positioned adjacent the two or more catalyst substrates, on a same side of the two or more substrates as the ultraviolet light source, on opposite sides of the ultraviolet light source and between the two or more catalyst substrates, each of the reflective surfaces having a shape such that the light from the ultraviolet light source strikes each of the reflective surfaces at a point and is reflected across the near surface of either the first or second catalyst substrate that is closest to the point at which the light struck either the first or second reflective surface.

2. The photocatalytic device of claim 1, wherein the hydrated multi-metallic catalyst further comprises one or more additional elements or compounds.

3. The photocatalytic device of claim 2, wherein the one or more additional elements or compounds comprise at least one of Carbon and Fluoride.

4. The photocatalytic device of claim 1, wherein the two or more catalyst substrates comprises a hydrated quad-metallic catalyst having four elements or compounds selected from the group: Titanium dioxide, Titanium, Platinum, Gold, Silver, Copper, Rhodium, Ruthenium, Lanthanum, Carbon, and Fluoride, with one or more of the four compounds or elements selected from the group: Titanium dioxide, Platinum, Gold, Silver, Copper, Rhodium, and with one or more of the four compounds or elements selected from the element group: Titanium, Ruthenium, and Lanthanum.

5. The photocatalytic device of claim 1, wherein the two or more catalyst substrates comprises a hydrated quintuple-metallic catalyst having five elements or compounds selected from the group: Titanium dioxide, Titanium, Platinum, Gold, Silver, Copper, Rhodium, Ruthenium, Lanthanum, Carbon, and Fluoride, with one or more of the five compounds or elements selected from the group: Titanium dioxide, Platinum, Gold, Silver, Copper, Rhodium, and with one or more of the five compounds or elements selected from the element group: Titanium, Ruthenium, and Lanthanum.

6. The photocatalytic device of claim 1, wherein the two or more catalyst substrates comprises a hydrated sextuple-metallic catalyst having six elements or compounds selected from the group: Titanium dioxide, Titanium, Platinum, Gold, Silver, Copper, Rhodium, Ruthenium, Lanthanum, Carbon, and Fluoride, with one or more of the six compounds or elements selected from the group: Titanium dioxide, Platinum, Gold, Silver, Copper, Rhodium, and with one or more of the six compounds or elements selected from the element group: Titanium, Ruthenium, and Lanthanum.

7. The photocatalytic device of claim 1, wherein the two or more catalyst substrates comprises a hydrated multi-metallic catalyst having at least five elements or compounds selected from the group: Titanium dioxide, Titanium Platinum, Gold, Silver, Copper, Rhodium, Ruthenium, Lanthanum, Carbon, and Fluoride, with one or more of the five compounds or elements selected from the group: Titanium dioxide, Platinum, Gold, Silver, Copper, Rhodium, and with one or more of the five compounds or elements selected from the element group: Titanium, Ruthenium, and Lanthanum.

8. The photocatalytic device of claim 1, wherein the first and second reflective surfaces comprise first and second convex reflectors having a shape adapted to distribute reflected light from the ultraviolet light source across the near surfaces of the first and second catalyst substrates.

9. The photocatalytic device of claim 1, further comprising at least one other reflective surface, each positioned adjacent the catalyst substrates on a side of a respective one of the substrates opposite the ultraviolet light source, each of the at least one other reflective surfaces having a shape reflecting ultraviolet light passing through the respective substrate onto a face of the respective substrate opposite the ultraviolet light source.

10. The photocatalytic device of claim 1, further comprising: a cylindrical shaped housing having an inlet opening and an outlet opening.

11. The photocatalytic device of claim 10, further comprising:

a fan disposed within the cylindrical housing and adapted to cause air to enter the cylindrical housing via the inlet opening, circulate through the two or more catalyst substrates, and exit the cylindrical housing via the outlet opening.

12. The photocatalytic device of claim 10, wherein the hydrated multi-metallic catalyst further comprises one or more additional elements or compounds.

13. The photocatalytic device of claim 12, wherein the one or more additional elements or compounds comprise at least one of Carbon and Fluoride.

14. The photocatalytic device of claim 10, wherein the two or more catalyst substrates comprise a cylindrical catalyst substrate.

15. The photocatalytic device of claim 10, further comprising:
one or more other reflective surface, each positioned adjacent the two or more catalyst substrates on a side of a respective one of the two or more catalyst substrates opposite the ultraviolet light source, each of the one or more other reflective surfaces having a shape adapted to reflect light passing through the respective substrate onto a face of the respective substrate opposite the ultraviolet light source.

16. A method of manufacturing a photocatalytic device, comprising:
providing an ultraviolet light source;
providing a first catalyst substrate and a second catalyst substrate, wherein the catalyst substrates are adapted to support a hydroxyl radical reaction with ultraviolet light and water vapor that results in hydro peroxides and hydroxyl ions, wherein the catalyst substrates comprise a hydrated multi-metallic catalyst having five or more elements or compounds selected from the group: Titanium dioxide, Titanium, Platinum, Gold, Silver, Copper, Rhodium, Ruthenium, and Lanthanum;
providing a first convex reflector and second convex reflector;
positioning the first and second catalyst substrates such that, in a cross-section of the photocatalytic device, the first and second catalyst substrates are in a parallel configuration with respect to each other;
positioning the first and second convex reflectors such that, in a cross-section of the photocatalytic device, the first and second convex reflectors are in a parallel configuration with respect to each other and in a perpendicular configuration with respect to the first and second catalyst substrates;
positioning the ultraviolet light between first and second convex reflectors and between the first and second catalyst substrates, the convex reflectors having a shape that such that the light from the ultraviolet light source strikes each of the convex reflectors at a point and is reflected across a near surface of either the first or second catalyst substrates that is closest to the point at which the light struck either the first or second convex reflector.

17. The method of claim 16, wherein the hydrated multi-metallic catalyst further comprises one or more additional elements or compounds.

18. The method of claim 17, wherein the one or more additional elements or compounds comprise at least one of Carbon and Fluoride.

19. The method of claim 16, further comprising positioning a reflective surface on a side of each of the substrates opposite the ultraviolet light source, such that each reflective surface reflects ultraviolet light passing through a respective substrate onto a face of the respective substrate opposite the ultraviolet light source.

* * * * *

UNITED STATES PATENT AND TRADEMARK OFFICE
CERTIFICATE OF CORRECTION

| | | |
|---|---|---|
| PATENT NO. | : 9,782,510 B1 | Page 1 of 1 |
| APPLICATION NO. | : 13/745132 | |
| DATED | : October 10, 2017 | |
| INVENTOR(S) | : Gregg William Burnett | |

It is certified that error appears in the above-identified patent and that said Letters Patent is hereby corrected as shown below:

In the Claims

In Column 10, Line 16, Claim 16, delete the 1st "that".

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*